United States Patent [19]

Barnett et al.

[11] 4,136,166

[45] Jan. 23, 1979

[54] SKIN LIGHTENING COMPOSITION

[75] Inventors: Gabriel Barnett, New York; Nathan Gershaw, Commack; Jack J. Mausner, East Hills, all of N.Y.

[73] Assignee: Helena Rubinstein, Inc., New York, N.Y.

[21] Appl. No.: 788,440

[22] Filed: Apr. 18, 1977

[51] Int. Cl.$^2$ ............................................. A61K 7/135
[52] U.S. Cl. ....................................... 424/62; 424/59; 424/60
[58] Field of Search .............................. 424/60, 62, 59

[56] References Cited

U.S. PATENT DOCUMENTS

| 2,274,725 | 3/1942 | Meeker et al. | 424/59 |
| 2,376,884 | 5/1945 | Schwenk et al. | 424/59 |
| 2,377,188 | 5/1945 | Schwenk et al. | 424/59 |
| 3,206,364 | 9/1965 | Purlee | 424/62 |
| 3,403,207 | 9/1968 | Kreps et al. | 424/60 |
| 3,485,915 | 12/1969 | Gerstein et al. | 424/60 |
| 3,856,934 | 12/1974 | Kligman | 424/62 |

FOREIGN PATENT DOCUMENTS

| 6505119 | 11/1965 | Netherlands | 424/62 |
| 1224145 | 3/1971 | United Kingdom | 424/62 |

OTHER PUBLICATIONS

Drug & Cosmetic Industry, 12/1968, pp. 40 to 44 & 153 & 154, vol. 103, No. 6.

Primary Examiner—Dale R. Ore
Attorney, Agent, or Firm—Burgess, Ryan and Wayne

[57] ABSTRACT

A skin lightener based on stabilized hydroquinone in a moisturizing base which also contains a sunscreen agent.

3 Claims, No Drawings

SKIN LIGHTENING COMPOSITION

BACKGROUND OF THE INVENTION

This invention relates to a cosmetic composition and, more particularly, this invention relates to a skin lightening composition.

Skin lighteners are known in the art and serve a useful purpose in the repertoire of cosmetics. They are usually gentle acting and are used on a localized area of the skin to "bleach" dark or blotchy areas which commonly form on the skin of elderly people.

A serious disadvantage of the prior art skin lighteners is the necessity to keep the skin shielded from the rays of the sun after use of the preparation. It is well known that excessive exposure to the sun or other ultraviolet radiation, even for a relatively short period of time, after use of a skin lightening preparation, could result in harmful side effects usually associated with overexposure to the sun.

SUMMARY OF THE INVENTION

It is, therefore, a primary object of the present invention to provide a skin lightening composition which is gentle acting and with which the user may be exposed to the sun after use.

It is another object of the present invention to provide a skin lightening composition which includes means for screening the harmful rays of the sun.

Consistent with these objects, and others which will become apparent as the description of the invention, a composition is provided which includes a stabilized hydroquinone "bleaching" agent and a sunscreen agent in a gentle cosmetic base. The cosmetic base generally comprises an emulsion of an oil phase and a water phase. The oil phase comprises an emollient. Emollients are organic substances having a boiling point higher than water and these substances remain on the skin as a vehicle for the critical blend of dyes. Suitable emollients for the present invention include, but are not limited to, aliphatic alcohols having 4 to 20 carbon atoms, glycols having 2 to 3 carbon atoms, fatty acids having from 12 to 20 carbon atoms and the esters thereof. These emollients are, for example, isostearyl alcohol, stearic acid, glyceryl monostearate, cetyl alcohol, isopropyl lanolate, isopropyl myristate, isopropyl palmitate and the like.

To enhance applicability onto the skin, small amounts of surfactants are included in the present cosmetic preparation. These include, for example, nonionic surfactants such as polyoxyethylene esters or ethers or other suitable surfactants known in the emulsion art. See, for example, McCutcheon, "Detergents and Emulsifiers" (1964).

The water phase also includes an emollient as well as other ingredients whose functions are apparent to one skilled in the art. Such ingredients are chelating agents such as EDTA and citric acid. Other such additives are preservatives to prevent microbial contamination. Such preservatives illustratively are the alkyl esters of p-hydroxybenzoic acid such as, for example, propyl paraben, methyl paraben, and anti-oxidants such as butylated hydroxyanisole compositions. Protective colloids and thickeners may also be included.

The vehicle is produced by mixing together these selected emollients, preservatives, anti-oxidants, and surfactants by simple but thorough blending. More specifically, the ingredients of the water phase and the oil phase are separately mixed and then the phases are combined. The skin lightening active ingredient, hydroquinone, is initially dissolved in the water phase and the sunscreen agent, which may be any conventional sunscreen agent such as 2-ethoxyethyl p-methoxycinnamate or amyl p-dimethylaminobenzoate, in the oil phase. The oil phase preferably also contains mineral oil.

DESCRIPTION OF THE PREFERRED EMBODIMENT

Having described the invention in more general terms, the following illustrative examples are provided for a better understanding of the practice of the instant invention. It is to be distinctly understood that the examples are in no way limiting.

EXAMPLE 1

The composition of the instant invention is made up of the following ingredients in the proportions shown, in percent by weight:

| Phase A | |
|---|---|
| Cetyl Alcohol | 0.25–8.00 |
| Myrj 52 (polyoxyethylene(40)stearate) | 0.25–5.00 |
| Brij 52 (polyoxyethylene(2)cetyl ether) | 0.25–5.00 |
| Marcol 70 (white mineral oil) | 2.00–35.00 |
| Tenox 2 (a composition of 20% butylated hydroxyanisole, 6% propyl gallate, and 4% citric acid in propylene glycol) | 0.05 |
| Stearic acid | 0.25–5.00 |
| Escalol 507(2-ethylhexyl-p-dimethylaminobenzoate) | 0.25–5.00 |
| Phase B | |
| Propylene glycol | 1.00–15.00 |
| Germall 115 (imidazolidinyl urea) | 0.35 |
| Methyl paraben | 0.15 |
| Cellosize WP-4400-L (hydroxyethylcellulose) | 0.25–3.50 |
| Veegum K (magnesium aluminum silicate) | 0.25–3.50 |
| Sequestrene Na2 (disodium ethylenediaminetetraacetic acid) | 0.05–1.00 |
| Citric acid (20% aq. sol'n) | 0.10–1.00 |
| Hydroquinone (USP) | 0.10–4.00 |
| Deionized water | qs. 100 |
| Phase C | |
| Sodium sulfite (AR) | 0.05–2.50 |
| Sodium metabisulfite (AR) | 0.05–2.50 |
| Deionized water | qs. 100 |
| Perfume C71-323 | 0.20 |

To make the composition, the water of Phase B is first placed in a stainless steel, steam-jacketed kettle equipped with a Lightnin' Mixer and counter-rotating mixers. The Lightnin' Mixer is started to provide fairly vigorous stirring, and the Veegum is sprinkled in and allowed to completely hydrate.

The methyl paraben is dissolved in the propylene glycol in a separate vessel and the Cellosize added to the propylene glycol mixture. The propylene glycol mixture is stirred well to disperse the Cellosize and then added to the Veegum-water mixture. The Germall and Sequestrene are added to the kettle and dissolved.

Phase A is made in a separate stainless steel, steam-jacketed kettle by adding all of the ingredients of Phase A and mixing.

Both phases are then heated to 75° C.

In the meantime, the sodium sulfite and the sodium metabisulfite are dissolved in the water for Phase C.

When Phase A (the water phase) is at 50° C., the citric acid solution is added followed by the hydroquinone and, finally, by Phase C.

When both Phases A and B are at 75° C., using counter-rotating mixers, the oil phase (Phase A) is strained through nylon cloth into the water phase (Phase B).

The combined phases are stirred for 10 minutes and then cooled. When the mixture is at 50° C., the perfume is added. The mixture is cooled to 30° C. and is ready for use.

EXAMPLE 2

A composition having the preferred proportion of ingredients was prepared following the procedure set forth in Example 1. The composition is as follows:

| Phase A | |
|---|---|
| Cetyl Alcohol | 4.0 |
| Myrj 52 (polyoxyethylene(40)stearate) | 1.25 |
| Brij 52 (polyoxyethylene(2)cetyl ether) | 1.5 |
| Marcol 70 (white mineral oil) | 11.0 |
| Tenox 2 | 0.05 |
| (a composition of 20% butylated hydroxy- | |
| anisole, 6% propyl gallate, and 4% citric | |
| acid in propylene glycol) | |
| Stearic acid | 2.5 |
| Escalol 507 (2-ethylhexyl-p-dimethylaminobenzoate) | 2.0 |
| Phase B | |
| Propylene glycol | 6.0 |
| Germall 115 | 0.35 |
| Methyl paraben | 0.15 |
| Cellosize WP-4400-L (hydroxyethylcellulose) | 0.5 |
| Veegum K (magnesium aluminum silicate) | 0.75 |
| Sequestrene Na2 (disodium ethylenediamine- | 0.10 |
| tetraacetic acid) | |
| Citric acid (20% aq. sol'n) | 0.5 |
| Hydroquinone (USP) | 2.0 |
| Deionized water | qs. 100 |
| Phase C | |
| Sodium sulfite (AR) | 0.26 |
| Sodium metabisulfite (AR) | 0.17 |
| Deionized water | qs. 100 |
| Perfume C71-323 | 0.20 |

It will be appreciated by those skilled in the art that the hydroquinone is included as the active ingredient for "bleaching" the skin. Since hydroquinone is a reducing agent, and oxidizes freely in air, the sodium sulfite and sodium metabisulfite are included as stabilizers. Since these latter ingredients have a greater affinity for the oxygen than does hydroquinone, they prevent oxidation of the hydroquinone.

Having described the invention by reference to the illustrative examples, it will be appreciated that the objects set forth at the outset have been successfully achieved. It is clearly understood that the scope of the invention is not to be limited by the exemplary matter but is only limited by the appended claims.

What is claimed is:

1. A skin lightening cosmetic composition, comprising, in parts by weight:

| A) | cetyl alcohol | 0.25 – 8.00 |
|---|---|---|
| | polyoxyethylene(40)stearate | 0.25 – 5.00 |
| | polyoxyethylene(2)cetyl ether | 0.25 – 5.00 |
| | white mineral oil | 2.00 – 35.00 |
| | preservative | effective amount |
| | stearic acid | 0.25 – 5.00 |
| | amyl p-dimethylaminobenzoate | 0.25 – 5.00 |
| B) | propylene glycol | 1.00 – 15.00 |
| | preservative | effective amount |
| | hydroxyethylcellulose | 0.25 – 3.50 |
| | magnesium aluminum silicate | 0.25 – 3.50 |
| | ethylenediaminetetraacetic acid | |
| | disodium salt | 0.05 – 1.00 |
| | citric acid (20% aq. sol'n) | 0.10 – 1.00 |
| | hydroquinone | 0.10 – 4.00 |
| | water | qs. 100 |
| C) | sodium sulfite | 0.05 – 2.50 |
| | sodium metabisulfite | 0.05 – 2.50 |
| | water | qs. 100. |

2. A composition as claimed in claim 1, wherein said preservative in phase (A) is 0.05 parts of a mixture of butylated hydroxyanisole, propyl gallate, and citric acid in propylene glycol.

3. A composition as claimed in claim 1, comprising, in parts by weight:

| A) | cetyl alcohol | 4.0 |
|---|---|---|
| | polyoxyethylene(40)stearate | 1.25 |
| | polyoxyethylene(2)cetyl ether | 1.5 |
| | white mineral oil | 11.0 |
| | butylated hydroxyanisole | effective amount |
| | stearic acid | 2.5 |
| | amyl p-dimethylaminobenzoate | 2.0 |
| B) | propylene glycol | 6.0 |
| | imidazolidinyl urea | 0.35 |
| | methyl paraben | 0.15 |
| | hydroxyethyl cellulose | 0.5 |
| | magnesium aluminum silicate | 0.75 |
| | ethylenediaminetetraacetic acid | |
| | disodium salt | 0.10 |
| | citric acid | 0.5 |
| | hydroquinone | 2.0 |
| | water | qs. 100 |
| C) | sodium sulfite | 0.26 |
| | sodium metabisulfite | 0.17 |
| | water | qs. 100 |
| D) | perfume | 0.20. |

* * * * *

UNITED STATES PATENT OFFICE
CERTIFICATE OF CORRECTION

Patent No. 4,136,166　　　　　　　　　Dated　January 23, 1979

Inventor(s)　Gabriel Barnett, & al

It is certified that error appears in the above-identified patent and that said Letters Patent are hereby corrected as shown below:

Column 2, line 6:　Change "amyl" to --2-ethylhexyl--.

Column 4, line 12:　Change "amyl" to --2-ethylhexyl--.

Column 4, line 34:　Change "amyl" to --2-ethylhexyl--.

Signed and Sealed this

Twenty-fourth Day of July 1979

[SEAL]

Attest:

LUTRELLE F. PARKER
　　　　Attesting Officer　　Acting Commissioner of Patents and Trademarks